US007754691B1

(12) United States Patent
Sharma

(10) Patent No.: US 7,754,691 B1
(45) Date of Patent: *Jul. 13, 2010

(54) LINEAR MELANOCORTIN RECEPTOR-SPECIFIC PEPTIDES FOR CACHEXIA

(75) Inventor: Shubh D. Sharma, Cranbury, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 991 days.

This patent is subject to a terminal disclaimer.

(21) Appl. No.: 11/428,749

(22) Filed: Jul. 5, 2006

Related U.S. Application Data

(60) Provisional application No. 60/697,601, filed on Jul. 7, 2005.

(51) Int. Cl.
*A61K 38/07* (2006.01)
*A61K 38/08* (2006.01)

(52) U.S. Cl. .............................. 514/16; 514/17; 514/18; 530/329; 530/330

(58) Field of Classification Search ....................... None
See application file for complete search history.

(56) References Cited

U.S. PATENT DOCUMENTS

| 5,731,408 | A | 3/1998 | Hadley et al. |
| 5,908,609 | A | 6/1999 | Lee et al. |
| 5,908,825 | A | 6/1999 | Fasano et al. |
| 5,932,779 | A | 8/1999 | Lee et al. |
| 5,977,070 | A | 11/1999 | Piazza et al. |
| 5,994,087 | A | 11/1999 | Cone et al. |
| 6,054,556 | A | 4/2000 | Huby et al. |
| 6,100,048 | A | 8/2000 | Cone et al. |
| 6,284,729 | B1 | 9/2001 | Bernfield et al. |
| 6,476,187 | B1 | 11/2002 | Cone et al. |
| 6,613,874 | B1 | 9/2003 | Mazur et al. |
| 6,693,165 | B2 | 2/2004 | Bednarek |
| 6,699,873 | B1 | 3/2004 | Maguire et al. |
| 6,716,810 | B1 | 4/2004 | Brennan |
| 2002/0016291 | A1 | 2/2002 | Bednarek |
| 2003/0032791 | A1 | 2/2003 | Alan et al. |
| 2003/0105024 | A1 | 6/2003 | Cone et al. |
| 2003/0113263 | A1 | 6/2003 | Marks et al. |
| 2004/0138136 | A1 | 7/2004 | Sharma et al. |
| 2005/0038230 | A1 | 2/2005 | Sharma et al. |
| 2005/0164914 | A1 | 7/2005 | Sharma et al. |
| 2005/0239711 | A1 | 10/2005 | Chen et al. |
| 2006/0014194 | A1 | 1/2006 | Sharma et al. |
| 2006/0014676 | A1 | 1/2006 | Sharma et al. |

FOREIGN PATENT DOCUMENTS

| WO | WO 98/56914 | 12/1998 |
| WO | WO 00/05385 | 2/2000 |
| WO | WO 01/13112 | 2/2001 |
| WO | WO 03/006620 | 1/2003 |
| WO | WO 2005/014617 | 2/2005 |
| WO | WO 2005/030797 | 4/2005 |
| WO | WO 2005/060985 | 7/2005 |

OTHER PUBLICATIONS

Zhenhai et al. 'Agonst-Dependent Internalization of the Human Melaocortin-4 Receptors in Human Embryonic Kidney 293 Cells.' J. of Pharm. & Exper. Therap. vol. 307, No. 3, pp. 870-877. 2003.*
Colombo et al. 'Structure-Activity Relationship of Linear and Cyclic Peptides Containing the NGR Tumar Homing Motif.' J. of Biol. CHem. vol. 277, No. 49, pp. 47891-47897. Dec. 2002.*
Bogdanowich-Knipp et al. 'Soluation Stability of Linear vs. Cyclic RGD Peptides.' J. Peptide Res. vol. 53, pp. 530-541. 1999.*
Wels et al. Synthesis of a Noval Potent Cyclic Peptide MC4 Ligand by Ring Closing Metathesis. Bioorganic & Medicinal Chem. vol. 13, pp. 4221-4227. May 2005.*
Seeley, R., "The Role of CNS Glucagon-Like Peptide-1; Amide Receptors in Mediating the Visceral Illness Effects of Lithium Chloride", J. of Neurosciences, vol. 20(4) 1616-1621.
Toniolo, C., "Conformationally restricted peptides through short-range cyclizations", Int. J. Peptide Protein Res., vol. 35 (1990) 287-300.
Wisse, Brent E., "Reversal of Cancer Anorexia by Blockade of Central Melanocortin Receptors in Rats", Endocrinology, vol. 142, No. 8 (2001) 3292-3301.
Catania, Anna, "a-Melanocyte-stimulating Hormone in Normal Human Physiology and Diease States", Trends Endocrinol. Metab. (TEM), vol. 11, No. 8, (2000), 304-308.
Fan, Wei, "Role of Melanocortinergic Neurons in Feeding and the Agouti Obesity Syndrome", Nature, vol. 385, Letters to Nature, (Jan. 9, 1997), 165-168.
Gantz, Ira, "The Melanocortin System", Am J Physiol Endocrinol Metab 284, Minireview, (2003), E468-E474.
Grant, Gregory A., "Protein and Amino Acid Chemistry", Synthetic Peptides: A User's Guide, Washington University School of Medicine, (1992), 11-24.
Hruby, V., "Emerging approaches in the molecular design of receptor-selective peptide ligands: conformational, topographical and dynamic . . . ", Bio.J., (1990), V. 268, 249-262.
Lynch, Huszard D., et al., "Targeted disruption of the melanocortin-4 receptor results in obesity in mice", Cell, 88, (1997), 131-141.
Marks, Daniel L., "Role of the Central Melanocortin System in Cachexia", Cancer Research, vol. 61, (Feb. 15, 2001), 1432-1438.
Merrifield, Robert B., "Solid Phase Synthesis (Nobel Lecture)", Angewandte Chemie, vol. 24, No. 10, (Oct. 1985), 799-810.
Rossi, M., "A C-terminal fragment of Agouti-related protein increases feeding and antagonizes the effect of alpha-melanocyte . . . ", Endo., vol. 139, 10, 1998 4428-4431.
Roubenoff, Ronenn, "The Pathophysiology of Wasting in the Elderly", J. Neurosci., Clinical Trials for the Treatment of Secondary Wasting and Cachexia, 1999, S256-S259.

\* cited by examiner

*Primary Examiner*—Anish Gupta
(74) *Attorney, Agent, or Firm*—Stephen A. Slusher

(57) ABSTRACT

Linear peptides with a C-terminus —OH group that are specific for one or more melanocortin receptors, and which may be used in the treatment of melanocortin receptor-mediated disorders, including a variety of body weight disorders including cachexia, and for treatment of inflammation, immune disorders and other conditions, diseases and syndromes, and pharmaceutical compositions including such linear peptides.

13 Claims, No Drawings

SEQUENCE LISTING

<160> NUMBER OF SEQ ID NOS: 3

<210> SEQ ID NO 1
<211> LENGTH: 4
<212> TYPE: PRT
<213> ORGANISM: Artificial
<220> FEATURE:
<223> OTHER INFORMATION: C-terminus artificial melanocortin peptide
      sequence

<400> SEQUENCE: 1

Pro Pro Lys Asp
1

```
<210> SEQ ID NO 2
<211> LENGTH: 5
<212> TYPE: PRT
<213> ORGANISM: Artificial
<220> FEATURE:
<223> OTHER INFORMATION: C-terminus artificial melanocortin peptide
      sequence

<400> SEQUENCE: 2

Ala Pro Pro Lys Asp
1               5

<210> SEQ ID NO 3
<211> LENGTH: 4
<212> TYPE: PRT
<213> ORGANISM: Artificial
<220> FEATURE:
<223> OTHER INFORMATION: C-terminus artificial melanocortin peptide
      sequence

<400> SEQUENCE: 3

Ala Lys Pro Val
1
```

LINEAR MELANOCORTIN RECEPTOR-SPECIFIC PEPTIDES FOR CACHEXIA

CROSS-REFERENCE TO RELATED APPLICATIONS

This application claims priority to and the benefit under 35 USC §119(e) of U.S. Provisional Patent Application Ser. No. 60/697,607, entitled "Linear Melanocortin Receptor-Specific Peptides for Cachexia", filed on Jul. 7, 2005, incorporated here by reference.

BACKGROUND OF THE INVENTION

1. Field of the Invention (Technical Field)

The present invention relates to linear peptides with a C-terminus —OH group that are specific for one or more melanocortin receptors, and which may be used in the treatment of melanocortin receptor-mediated disorders, including a variety of body weight disorders such as cachexia, for treatment of inflammation and immune disorders, and other conditions and diseases.

2. Description of Related Art

Note that the following discussion refers to a number of publications by author(s) and year of publication, and that due to recent publication dates or priority claims certain publications or patent applications are not to be considered as prior art vis-a-vis the present invention. Discussion of such publications and applications herein is given for more complete background and is not to be construed as an admission that such publications or applications are prior art for patentability determination purposes.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, midbrain and brainstem, and melanocortin-5 receptors (MC5-R), expressed in a wide distribution of peripheral tissues.

Significant work has been done in determining the structure of melanocortin receptors, including both the nucleic acid sequences encoding for the receptors and the amino acid sequences constituting the receptors. See, for example, International Patent Application Nos. PCT/US98/12098 and PCT/US99/16862 and U.S. Pat. No. 5,994,087. MC4-R is a G protein-coupled, 7-transmembrane receptor that is believed to be expressed primarily in the brain. Inactivation of this receptor by gene targeting has been reported to result in mice with the maturity-onset obesity syndrome that is associated with hyperphagia, hyperinsulinemia, and hyperglycemia (Huszar D, Lynch C A, Fairchild-Huntress V, et al. Targeted disruption of the melanocortin-4 receptor results in obesity in mice. *Cell* 88:131-141, 1997). MC4-R is a molecular target for therapeutic intervention in energy homeostasis.

A large number of ligands specific for melanocortin receptors, both agonists and antagonists, have been developed. See, for example, International Publication No. WO 01/13112 and U.S. Publication No. 2005/0164914 (metallopeptides specific for MC receptors); U.S. Pat. No. 6,054,556 (cyclic lactam peptides as MC1-R, MC3-R, MC4-R and MC5-R antagonists); U.S. Publication No. 2004/0138136 (cyclic peptides for treatment of sexual dysfunction); U.S. Publication No. 2005/0038230 (linear and cyclic melanocortin receptor-specific peptides); International Publication No. WO 2005/014617 (C-terminus —OH group cyclic peptides); U.S. Publication Nos. 2006/0014676 and 2006/0014194 (cyclic peptides for treatment of cachexia including one or more NaI amino acid residues); International Publication No. WO 2005/030797 (cyclic peptides optionally including a NaI amino acid residue); and U.S. Publication No. 2005/0239711 (MC4-R agonist linear peptides). In addition, a large number of patents teach various methods of screening and determining melanocortin receptor-specific compounds, as for example U.S. Pat. Nos. 5,932,779 and 5,994,087.

In general, compounds specific for MC3-R, MC4-R or MC5-R are believed to be useful in regulation of energy homeostasis, including use as agents for attenuating food intake and body weight gain, for use in treatment of cachexia, for use in treatment of anorexia, as a weight gain aid, for treatment of obesity, and other treatment of other food intake and metabolism-related purposes. Compounds specific for MC3-R and MC4-R, among other melanocortin receptors, can be used to regulate blood pressure, heart rate and other neurophysiologic parameters. MC4-R antagonists can be employed to alleviate numerous conditions such as anxiety/depression, pain, and addiction to drugs of abuse. In at least one report, MC4-R agonists are described as useful to inhibit or reduce voluntary alcohol consumption (International Publication No. WO 2005/060985).

Body weight disorders can include one or more "wasting" disorders (e.g., wasting syndrome, cachexia, sarcopenia) which cause undesirable and/or unhealthy loss of weight or loss of body cell mass. In the elderly as well as in cancer and AIDS patients, wasting disease can result in undesired loss of body weight, including both the fat and the fat-free compartments. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, extraintestinal Crohn's disease, psychogenic disease, chronic heart failure or other severe trauma, frequently suffer from wasting disease which is sometimes also referred to as cachexia, a metabolic and, sometimes, an eating disorder. Cachexia is additionally characterized by hypermetabolism and hypercatabolism. Although cachexia and wasting disease are frequently used interchangeably to refer to wasting conditions, there is at least one body of research which differentiates cachexia from wasting syndrome as a loss of fat-free mass, and particularly, body cell mass (Mayer, *J. Nutr.* 129(1S Suppl.): 256S-259S, 1999). Sarcopenia, yet another such disorder which can affect the aging individual, is typically characterized by loss of muscle mass. End stage wasting disease as described above can develop in individuals suffering from either cachexia or sarcopenia. Certain patents teach the use of melanocortin antagonists for treatment of cachexia and other weight-related disorders. See, for example, U.S. Pat. Nos. 6,716,810; 6,699,873; 6,693,165; 6,613,874; 6,476,187; 6,284,729; 6,100,048; and 5,908,609. However, none of these disclose the peptides of the present invention.

The cyclic peptide SHU9119 (Ac-Nle-cyclo(-Asp-His-D-NaI 2-Arg-Trp-Lys)-NH$_2$) is disclosed in U.S. Pat. No. 5,731,408. Related cyclic peptides are disclosed in U.S. Pat. No. 6,054,556. U.S. Publication No. 2003/0113263 discloses a method for characterizing a compound useful for treating an animal with cachexia, including use of an MC4-R antagonist to treat an animal with cachexia, and specifically disclosing SHU9119. U.S. Publication No. 2003/0105024 discloses SHU9119 as a MC receptor antagonist used experimentally to stimulate feeding behavior. U.S. Pat. No. 6,476,187 similarly discloses SHU9119 as a MC receptor antagonist used experimentally to stimulate feeding behavior. U.S. Publication No. 2003/0032791 discloses the experimental use of SHU9119 in various assays. U.S. Publication No. 2002/0016291 discloses SHU9119 as an antagonist at the MC3 and MC4 receptors. In 1997, it was disclosed that SHU9119 enhanced feeding behavior. Fan, Boston, Kester, Hruby, Cone: *Nature* 385:165-168, 1997; see also *Endrocrinology*, 139:4428-31, 1998; *Endrocrinology*, 142:3292-3301, 2001; and *Cancer Research*, 61:1432-1438, 2001.

There remains a significant need for peptides with high specificity for discrete melanocortin receptors, as well as peptides that are either antagonists or inverse agonists of specific melanocortin receptors. High affinity peptide ligands of melanocortin receptors can be used to exploit varied physiological responses associated with the melanocortin receptors, either as antagonists or inverse agonists. In one aspect, antagonists or inverse agonists of MC4-R can be used to treat eating disorders or cachexia. In addition, melanocortin receptors have an effect on the activity of various cytokines, and high affinity peptide ligands of melanocortin receptors can be used to regulate cytokine activity. Thus such peptides may further be used for treatment of inflammation and other immune disorders. In another aspect, MC4-R specific peptides can be used to treat anxiety/depression, pain, and addiction to drugs of abuse, including inhibition or reduction of alcohol consumption.

BRIEF SUMMARY OF THE INVENTION

In one embodiment, the invention provides a linear peptide of the formula:

Y-Xaa$_1$-Xaa$_2$-Xaa$_3$-Xaa$_4$-Z—OH  III or a pharmaceutically acceptable salt thereof,
wherein:
Y comprises from zero to about three L- or D-amino acid residues, optionally with an N-terminus capping group, or an N-terminus capping group;
Z comprises from zero to about seven L- or D-amino acid residues wherein the C-terminus is a free carboxylate group;
Xaa$_1$ and Xaa$_4$ are each independently an L- or D-amino acid with a side chain consisting of H, containing a C$_1$ to C$_6$ aliphatic linear or branched chain or containing an aromatic amino acid side chain moiety, on the proviso that at least one of Xaa$_1$ and Xaa$_4$ is an amino acid with an aromatic amino acid side chain moiety;
Xaa$_2$ is a D-amino acid with a naphthyl ring structure or a substituted phenyl ring, wherein the phenyl ring is substituted at the 4 position with an iodo group, a C$_1$ to C$_4$ branched or linear aliphatic chain optionally further comprising an ether linkage, or a phenyl ring and a bond or a phenyl ring and an ether linkage; and
Xaa$_3$ is an L- or D-amino acid with a C$_1$ to C$_6$ linear or branched chain amino acid side chain or a neutral hydrogen bonding or positively charged amino acid side chain.

In one aspect of the invention, in the compound of formula III Z comprises from zero to about five L- or D-amino acid residues. In one particular aspect, Z has two amino acid residues.

In another aspect of the invention, in the compound of formula III the N-terminus group of Y comprises an N-terminus acetyl group.

In another aspect of the invention, the compound of formula III has a total of four amino acid residues, five amino acid residues, six amino acid residues, or seven amino acid residues.

In another aspect of the invention, in the compound of formula III Y has two amino acid residues, and in yet another aspect, two amino acid residues and an N-terminus capping group. In one aspect, the N-terminus capping group is acetyl.

Compounds of the invention thus include compounds wherein Xaa$_1$ is His, Pro, Tyr, Trp, Phe, NaI 1 or NaI 2.

Compounds of the invention further include compounds wherein Xaa$_2$ is D-NaI 2. In a further embodiment of the invention, Xaa$_2$ is D-Phe(4-I), D-Phe(3,4-di-OMe), D-Phe(4-Me), or D-Phe(4-OMe). The compounds of the invention also include compounds wherein Xaa$_2$ is D-Phe substituted at the 4 position with one of the following substituents:

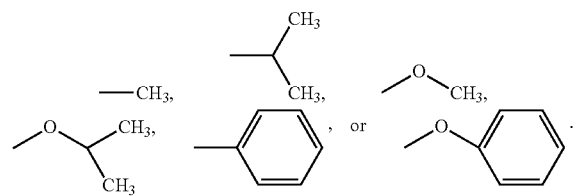

Compounds of the invention further include compounds wherein Xaa$_3$ is Arg, Lys, Orn, Leu or Nle.

In another aspect of the invention, Arg is an L- or D-isomer of Arg, Arg(NO$_2$), Arg(Tos), Arg(Pbf), Arg(Mtr), Arg(Me), or Arg(Pmc).

Compounds of the invention further include compounds wherein Xaa$_4$ is Trp, NaI 1, NaI 2 or Phe.

In one aspect, Y comprises the sequence Nle-Arg.

In another aspect, Z comprises the sequence Pro-Pro-Lys-Asp (SEQ ID NO: 1), Ala-Pro-Pro-Lys-Asp (SEQ ID NO: 2), Lys-Pro-Val, or Ala-Lys-Pro-Val (SEQ ID NO: 3).

The compounds of the invention thus include any of the following linear peptides:
Ac-Nle-Ala-His-D-NaI 2-Arg-Trp-Lys-OH;
Ac-Ala-His-D-NaI 2-Arg-Trp-Lys-OH;
Ac-Nle-Ala-Trp-D-NaI 2-Arg-NaI 2-Lys-OH;
Ac-Ala-Trp-D-NaI 2-Arg-NaI 2-Lys-OH;
Ac-Nle-Ala-His-D-NaI 2-Arg-NaI 2-Lys-OH;
Ac-Ala-His-D-NaI 2-Arg-NaI 2-Lys-OH;
Nle-Ala-His-D-NaI 2-Arg-Trp-Lys-OH;
Ala-His-D-NaI 2-Arg-Trp-Lys-OH;
Nle-Ala-Trp-D-NaI 2-Arg-NaI 2-Lys-OH;
Ala-Trp-D-NaI 2-Arg-NaI 2-Lys-OH;
Nle-Ala-His-D-NaI 2-Arg-NaI 2-Lys-OH;
Ala-His-D-NaI 2-Arg-NaI 2-Lys-OH;
Succ-His-D-NaI 2-Arg-NaI 2-Lys-OH.
Ac-Glu-His-D-NaI 2-Arg-Trp-Lys-Pro-Val-OH;
Ac-Glu-His-D-NaI 2-Arg-Trp-OH;
Ac-Glu-Pro-D-NaI 2-Arg-Trp-OH;
Ac-Ala-Nle-Arg-His-D-NaI 2-Arg-Trp-Gly-OH;
Nle-Arg-His-D-NaI 2-Arg-Trp-Gly-OH;
Ac-Glu-His-D-NaI 2-Arg-Trp-Pro-Pro-Lys-Asp-OH;
Ac-Glu-Pro-D-NaI 2-Arg-Trp-Pro-Pro-Lys-Asp-OH;
Ac-His-D-NaI 2-Arg-Trp-OH;
Ac-His-D-NaI 2-Arg-Trp-Lys-OH;
Ac-Trp-D-NaI 2-Arg-NaI 2-OH;
Ac-Trp-D-NaI 2-Arg-NaI 2-Lys-OH;
Ac-His-D-NaI 2-Arg-NaI 2-OH;
Ac-His-D-NaI 2-Arg-NaI 2-Lys-OH;
Ac-Pro-D-NaI 2-Arg-NaI 2-OH;
Ac-Pro-D-NaI 2-Arg-NaI 2-Lys-OH;
His-D-NaI 2-Arg-Trp-OH;
His-D-NaI 2-Arg-Trp-Lys-OH;
Trp-D-NaI 2-Arg-NaI 2-OH;

Trp-D-NaI 2-Arg-NaI 2-Lys-OH;
His-D-NaI 2-Arg-NaI 2-OH;
His-D-NaI 2-Arg-NaI 2-Lys-OH;
Pro-D-NaI 2-Arg-NaI 2-OH;
Pro-D-NaI 2-Arg-NaI 2-Lys-OH; or
Succ-His-D-NaI 2-Arg-NaI 2-OH.

In one aspect of the invention there is provided a pharmaceutical preparation, comprising a linear peptide of this invention and a pharmaceutically acceptable carrier.

The invention further comprises a method for increasing weight gain in a mammal, comprising administering a pharmaceutically sufficient amount of a composition comprising a peptide or pharmaceutically acceptable salt thereof, and particularly an MC4-R selective antagonist or inverse agonist. The method may further comprise a pharmaceutically acceptable carrier. In the method, administering may include administering by a method of administration such as administration by injection, administration through mucous membranes, buccal administration, oral administration, dermal administration, inhalation administration, nasal administration, parenteral administration, pulmonary administration, ocular administration and sublingual administration. In the event of nasal administration, it may be nasal administration of a metered amount of a formulation comprising an aqueous buffer. The method may further include a time release formulation, such that a pharmaceutically sufficient amount of a composition comprising a peptide or pharmaceutically acceptable salt thereof in a time release formulation is administered by injection or implantation.

A second object of the present invention is to provide a C-terminus free acid peptide-based melanocortin receptor-specific pharmaceutical for use in treatment of cachexia.

Another object of this invention is to provide compounds which are specific for melanocortin receptor MC4-R and which are partial agonists, antagonists or inverse agonists.

Another object of the present invention is a peptide-based melanocortin receptor-specific pharmaceutical for use in treatment of inflammation and other immune related disorders.

Another object of the present invention is a peptide-based melanocortin receptor-specific pharmaceutical for use in treatment of anxiety/depression, pain, and addiction to drugs of abuse, including inhibition or reduction of alcohol consumption.

Yet another object is to provide a melanocortin receptor-specific pharmaceutical for use in treatment of which is effective by nasal administration.

Yet another object is to provide a melanocortin receptor-specific pharmaceutical for use in treatment of which is effective when administered by an injectable or implantable time release formulation.

In one embodiment, an advantage of the present invention is that it provides a C-terminus free acid peptide-based melanocortin receptor-specific pharmaceutical for use in treatment of eating disorders which is efficacious at low doses.

Another advantage of the present invention is that it provides in one embodiment a C-terminus free acid peptide-based melanocortin receptor-specific pharmaceutical that is effective over a significant dose range, without deleterious side effects.

Yet another advantage of the present invention is that it provides a C-terminus free acid peptide-based melanocortin receptor-specific pharmaceutical for use in treatment of eating disorders which, because of increased efficacy at low doses, may be administered by delivery systems other than art conventional intravenous, subcutaneous or intramuscular injection, including but not limited to oral delivery systems, nasal delivery systems mucous membrane delivery systems and time release systems, either injectable or implantable.

Other objects, advantages and novel features, and further scope of applicability of the present invention will be set forth in part in the detailed description to follow, and in part will become apparent to those skilled in the art upon examination of the following, or may be learned by practice of the invention.

DESCRIPTION OF THE PREFERRED EMBODIMENTS

Best Modes for Carrying Out the Invention

Definitions. Certain terms as used throughout the specification and claims are defined as follows.

The terms "bind," "binding," "complex," and "complexing," as used throughout the specification and claims, are generally intended to cover all types of physical and chemical binding, reactions, complexing, attraction, chelating and the like.

The "peptides" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. For the most part, the peptides of this invention comprise fewer than 100 amino acids, and preferably fewer than 60 amino acids, and most preferably ranging from about 4 to about 10 amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition. A "derivative" of an amino acid side chain moiety is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

Homologs of the peptide include those sequences with a single amino acid substitution at any location. In one embodiment of the invention, the substitution is made by any of the naturally occurring amino acids or unnaturally occurring amino acids. Homologs of the peptide may also include those sequences where one amino acid with an aromatic ring has been substituted for another amino acid with a different aromatic ring. An example of this substitution would be replacing a Phe residue with a Trp residue. Homologs of the peptide may also include those sequences where an amino acid with a charged side chain is replaced by another amino acid with or without a charged side chain. Examples of this include, without limitation, replacing an Arg residue (positively charged side chain) with a Lys (positively charged side chain) or replacing a H is (positively charged side chain) with a Phe (nonpolar side chain).

The "amino acids" used in this invention, and the term as used in the specification and claims, include the known naturally occurring protein amino acids, which are referred to by both their common three letter abbreviation and single letter abbreviation. See generally Synthetic Peptides: A User's Guide, G A Grant, editor, W.H. Freeman & Co., New York (1992), the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in Synthetic Peptides: A User's Guide, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference. In addition, the following abbreviations have the meanings giving:

| | |
|---|---|
| Arg(Me) | $N^G$-methyl-arginine |
| Arg(Mtr) | $N^G$-4 methoxy-2,3,6-trimethylbenzenesulfonyl-arginine |
| Arg(NO$_2$) | $N^G$-nitro-arginine |
| Arg(Pbf) | $N^G$-pentamethyldihydrobenzofuran-5-sulfonyl (Pbf) |
| Arg(Pmc) | $N^G$-2,2,5,7,8-pentamethylchromane-6-sulfonyl-arginine |
| Arg(Tos) | $N^G$-para-tosyl-arginine |
| Asp(3-Cl-anilino) | beta-(3-chloro-anilino)-aspartic acid |
| Asp(aniline) | beta-anilino-aspartic acid |
| Nal 1 | 3-(1-naphthyl)alanine |
| Nal 2 | 3-(2-naphthyl)alanine |
| Phe(3,4-di-OMe) | 3,4-dimethoxy-phenylalanine |
| Phe(4-I) | 4-iodo-phenylalanine |
| Phe(4-Me) | 4-methyl-phenylalanine |
| Phe(4-OMe) | 4-methoxy-phenylalanine |
| Succ | Succinic acid (dicarboxylic acid of molecular formula $C_4H_6O_4$) |

In the listing of compounds according to the present invention, conventional amino acid residues have their conventional meaning as given in Chapter 2400 of the *Manual of Patent Examining Procedure*, 8$^{th}$ Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, "Ser" is serine and so on.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A peptide or aliphatic moiety is "acylated" when an alkyl or substituted alkyl group as defined above is bonded through one or more carbonyl {—(C=O)—} groups. A peptide is most usually acylated at the N-terminus.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—CO.NH₂), such as for example methylamide, ethylamide, propylamide, and the like.

An "imide" includes compounds containing an imido group (—CO.NH.CO—).

An "amine" includes compounds that contain an amino group (—NH₂).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

The term "halogen" is intended to include the halogen atoms fluorine, chlorine, bromine and iodine, and groups including one or more halogen atoms, such as —CF₃ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound or peptide of the present invention and a pharmaceutically acceptable carrier.

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue."

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by a melanocortin receptor agonist agent. By a melanocortin receptor "inverse agonist" is meant a drug or a compound that stabilizes the inactive conformation of the melanocortin receptor and inhibits basal activity.

"Eating disorders" are those related to underweight, cachexia, anorexia or bulimia of any cause in humans.

"Cachexia" refers to a state of general ill health and malnutrition. It is often associated with and induced by malignant cancer, cystic fibrosis or AIDS, and is characterized by loss of appetite, loss of body mass, especially lean body mass, and muscle wasting.

"Anorexia" refers simply to a loss of appetite, whether brought on by medical, physiological or psychological factors. Anorexia is often closely associated with, and generally contributes to, the cachexia seen in patients with advanced cancers and other conditions.

Peptides of the Invention

In one embodiment the invention provides linear peptides which include the core sequence His-D-NaI 2-Arg-Trp, or homologs or analogs of the foregoing. In another embodiment the invention provides peptides which include the core sequence His-D-NaI 2-Arg-NaI 2, or homologs or analogs of the foregoing. The peptide is deamidated, which is to say that it does not include an —NH₂ group at the C-terminus. In a preferred embodiment, the deamidated α-MSH peptides of this invention have an —OH group at the C-terminus, and are thus a free acid form of peptide.

Most preferably the peptides bind to MC4-R with high affinity, with a Ki value of at least 100 nM, preferably of at least 10 nM and most preferably from about 0.1 nM to about 5 nM. In some embodiments the peptides are functionally inverse agonists with respect to such receptor or receptors. However, the peptides of this invention need not be inverse agonists. Such peptides can preferably be employed in the treatment of eating disorders, and may be characterized in part as inducing weight increase in mammals, including but not limited to rodents.

Peptides of the invention are, in one aspect, linear peptides of the formula:

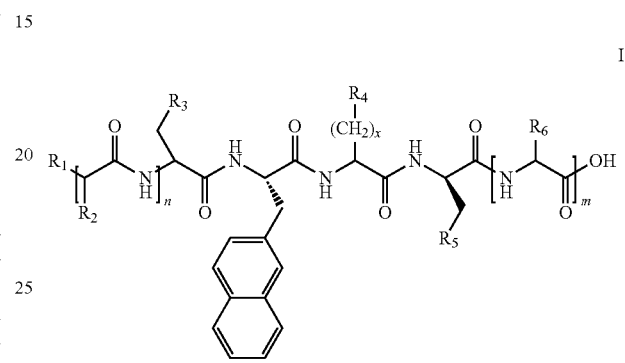

wherein:

$R_1$ is H, NH₂,

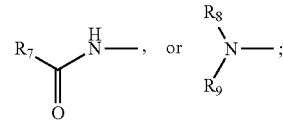

$R_2$ is in each instance independently an amino acid side chain moiety;

$R_3$ is 4-imidazolyl, 3-indolyl, 2-pyrrolidine, phenyl, or 1- or 2-naphthyl, optionally with one or two ring substituents, and when one or both ring substitutents are present, are the same or different and independently hydroxyl, halogen, alkyl, or aryl groups attached directly or through an ether linkage;

$R_4$ is —NH₂, —NH—(CH₂)$_y$—NH₂, or —NH—(C=NH)—NH₂;

$R_5$ is 1- or 2-naphthyl, optionally with one or two ring substituents, and when one or both ring substitutents are present, are the same or different and independently hydroxyl, halogen, alkyl, or aryl groups attached directly or through an ether linkage;

$R_6$ is in each instance independently H or an amino acid side chain moiety;

$R_7$ is H, NH₂, a lower aliphatic $C_1$ to $C_4$ linear or branched alkyl chain, a $C_1$ to $C_4$ aralkyl, or a $C_1$ to $C_4$ omega amino derivative;

$R_8$ is H, a lower aliphatic $C_1$ to $C_4$ linear or branched alkyl chain, a $C_1$ to $C_4$ aralkyl, a $C_1$ to $C_4$ linear alkyl chain with an N-terminus carboxyl group, or a $C_1$ to $C_4$ omega amino derivative;

$R_9$ is a linear or branched $C_1$ to $C_{17}$ alkyl, aryl, heteroaryl, alkene, alkenyl, or aralkyl chain;

n is from 0 to 3;

m is from 0 to 7;

x is 2 to 5; and y is 1 to 3.

In one aspect, $R_1$ is

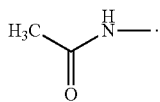

In another aspect, n is 0. In another aspect, n is 1 and $R_2$ is an amino acid side chain moiety of Nle, Ala, or Pro. In another aspect, n is 2 and $R_2$ is in each instance an amino acid side chain moiety of Nle, Ala, Arg, Pro, or a combination thereof.

In another aspect, $R_1$ is

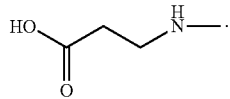

In one aspect wherein m is 1, $R_6$ is H or an amino acid side chain moiety of Lys. In another aspect wherein m is 2, $R_6$ is H or an amino acid side chain moiety of Lys or Trp or a combination thereof. In another aspect wherein m is 3 or 4, $R_6$ is H or an amino acid side chain moiety of Lys, Pro, Val, Asp or Trp or a combination thereof.

The linear peptides of formula I thus include the following peptides:

Ac-Nle-Ala-Trp-D-NaI 2-Arg-NaI 2-Lys-OH;
Ac-Ala-Trp-D-NaI 2-Arg-NaI 2-Lys-OH;
Ac-Nle-Ala-His-D-NaI 2-Arg-NaI 2-Lys-OH;
Ac-Ala-His-D-NaI 2-Arg-NaI 2-Lys-OH;
Nle-Ala-Trp-D-NaI 2-Arg-NaI 2-Lys-OH;
Ala-Trp-D-NaI 2-Arg-NaI 2-Lys-OH;
Nle-Ala-His-D-NaI 2-Arg-NaI 2-Lys-OH;
Ala-His-D-NaI 2-Arg-NaI 2-Lys-OH;
Succ-His-D-NaI 2-Arg-NaI 2-Lys-OH.
Ac-Trp-D-NaI 2-Arg-NaI 2-OH;
Ac-Trp-D-NaI 2-Arg-NaI 2-Lys-OH;
Ac-His-D-NaI 2-Arg-NaI 2-OH;
Ac-His-D-NaI 2-Arg-NaI 2-Lys-OH;
Trp-D-NaI 2-Arg-NaI 2-OH;
Trp-D-NaI 2-Arg-NaI 2-Lys-OH;
His-D-NaI 2-Arg-NaI 2-OH;
His-D-NaI 2-Arg-NaI 2-Lys-OH; or
Succ-His-D-NaI 2-Arg-NaI 2-OH.

In another aspect, there is provided a linear peptide of the formula:

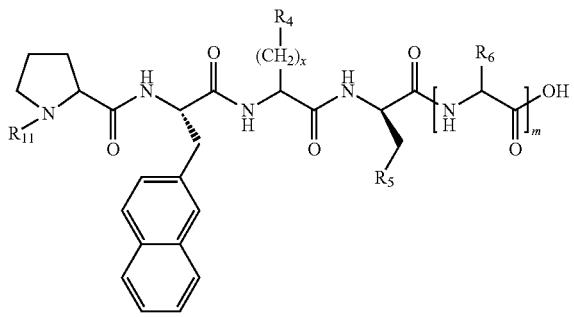

II wherein:
$R_{11}$ is H or

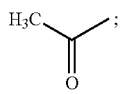

$R_4$ is $-NH_2$, $-NH-(CH_2)_y-NH_2$, or $-NH-(C=NH)-NH_2$;

$R_5$ is 1- or 2-naphthyl, optionally with one or two ring substitutents, and when one or both ring substitutents are present, are the same or different and independently hydroxyl, halogen, alkyl, or aryl groups attached directly or through an ether linkage;

$R_6$ is in each instance independently H or an amino acid side chain moiety;

m is from 0 to 7; and x is 2 to 5.

The linear peptides of formula II include the following peptides:

Ac-Pro-D-NaI 2-Arg-NaI 2-OH;
Ac-Pro-D-NaI 2-Arg-NaI 2-Lys-OH;
Pro-D-NaI 2-Arg-NaI 2-OH; or
Pro-D-NaI 2-Arg-NaI 2-Lys-OH.

Peptide Synthesis

The peptides of this invention may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group or other reactive groups protected and the free primary carboxyl group of another amino acid or residue thereof having its amino group or other reactive groups protected. In a preferred conventional procedure, the peptides of this invention may be synthesized by solid-phase synthesis and purified according to methods known in the art. Any of a number of well-known procedures utilizing a variety of resins and reagents may be used to prepare the peptides of this invention.

The process for synthesizing the peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Solid phase peptide synthesis methods are well known and practiced in the art. In such a method the synthesis of peptides of the invention can be carried out by sequentially incorporating the desired amino acid residues one at a time into the growing peptide chain according to the general principles of solid phase methods. These methods are disclosed in numerous references, including, Merrifield, R. B., Solid phase synthesis (Nobel lecture). *Angew Chem* 24:799-810 (1985) and Barany et al., *The Peptides, Analysis, Synthesis and Biology*, Vol. 2, Gross, E. and Meienhofer, J., Eds. Academic Press 1-284 (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pmc is a preferred protecting group for Arg.

The peptides of the invention described herein can be prepared using solid phase synthesis, such as by means of a Symphony Multiplex Peptide Synthesizer (Rainin Instrument Company) automated peptide synthesizer, using programming modules as provided by the manufacturer and following the protocols set forth in the manufacturer's manual.

Solid phase synthesis is commenced from the C-terminal end of the peptide by coupling a protected alpha amino acid to a suitable resin. Such a starting material can be prepared by attaching an alpha amino-protected amino acid by an ester linkage to a p-benzyloxybenzyl alcohol (Wang) resin or a 2-chlorotrityl chloride resin, by an amide bond between an Fmoc-linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art. Fmoc-linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in DMF may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Methods for N-terminus modification, such as acetylation, or C-terminus modification, such as deamidation, are well known in the art. Similarly, methods for modifying side chains of amino acids are well known to those skilled in the art of peptide synthesis. The choice of modifications made to reactive groups present on the peptide will be determined, in part, by the characteristics that are desired in the peptide.

Following cleavage of peptides from the solid phase following their synthesis, the peptide can be purified by any number of methods, such as reverse phase high performance liquid chromatography (RP-HPLC), using a suitable column, such as a $C_{18}$ column. Other methods of separation or purification, such as methods based on the size or charge of the peptide, can also be employed. Once purified, the peptide can be characterized by any number of methods, such as high performance liquid chromatograph (HPLC), amino acid analysis, mass spectrometry, and the like.

Formulation and Utility

The peptides disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

In general, the peptides of this invention may be synthesized by solid-phase synthesis and purified according to methods known in the art. Any of a number of well-known procedures utilizing a variety of resins and reagents may be used to prepare the compounds of this invention.

Salt Form of Peptides. The peptides of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptides of this invention are prepared in a suitable solvent from the peptide and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the peptides of this invention include an acidic moiety, suitable pharmaceutically acceptable salts may include alkali metal salts, such as sodium or potassium salts, or alkaline earth metal salts, such as calcium or magnesium salts.

Pharmaceutical Compositions. The invention provides a pharmaceutical composition that includes a peptide of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The peptide compositions of this invention may be formulated or compounded into pharmaceutical compositions that include at least one peptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

In general, the actual quantity of peptides of this invention administered to a patient will vary between fairly wide ranges depending on the mode of administration, the formulation used, and the response desired.

In practical use, the peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or non-aqueous techniques. The amount of active peptide in such therapeutically useful compositions is such that an effective dosage will be obtained. In another advantageous dosage unit form, sublingual constructs may be employed, such as sheets, wafers, tablets or the like. The active peptides can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Peptides may also be administered parenterally. Solutions or suspensions of these active peptides can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The peptides of this invention may be therapeutically applied by means of nasal administration. By "nasal administration" is meant any form of intranasal administration of any of the peptides of this invention. The peptides may be in an aqueous solution, such as a solution including saline, citrate or other common excipients or preservatives. The peptides may also be in a dry or powder formulation.

In an alternative embodiment, peptides of this invention may be administered directly into the lung. Intrapulmonary administration may be performed by means of a metered dose inhaler, a device allowing self-administration of a metered bolus of a peptide of this invention when actuated by a patient during inspiration.

The peptides of this invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the peptides may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the peptide may be in a dried and particulate form. In a preferred embodiment, the particles are between about 0.5 and 6.0 μm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 μm.

Microparticle size, including mean size distribution, may be controlled by means of the method of making. For micromilling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

In one preferred embodiment, a dry powder inhaler is employed which includes a piezoelectric crystal that deaggregates a dry powder dose, creating a small powder "cloud." Once the powder cloud is generated, an electricostatically charged plated above the powder cloud lifts the drug into the air stream. The user with one relatively easy breath can then inhale the powder. The device may be breath activated, utilizing a flow sensor that activates the electronic components upon the start of inhalation, and thereby eliminating the need for coordination of activation and breathing rhythms by the user.

The peptides of this invention may be therapeutically applied by means of an injection, typically deep intramuscular injection, such as in the gluteal or deltoid muscle, of a time release injectable formulation. Alternatively the peptides of this invention may be therapeutically applied by means of implantation of a time release injectable formulation. In one aspect the time release injectable formulation includes a peptide of this invention is formulated with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a peptide of this invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer is employed. In general, any of a number of injectable or implantable and bioerodible polymers, which are preferably also adhesive polymers, may be employed in a time release formulation. The formulation may be such that an injection or other implantation is required on a weekly, monthly or other periodic basis, depending on the concentration and amount of peptide, the bioerosion rate of the polymer, and other factors known to those of skill in the art.

Routes of Administration. If it is administered by injection, the injection may be intravenous, subcutaneous, intramuscular, intraperitoneal or other means known in the art. The peptides of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

Therapeutically Effective Amount. In general, the actual quantity of peptide of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptide or pharmaceutical composition of this invention that is sufficient to therapeutically alleviate feeding disorder in a patient, or to prevent or delay onset or recurrence of the feeding disorder, or for the management of the feeding disorder in patients with diseases or syndromes associated with cachexia, including secondary to immune disorders and cancer.

In general, the peptides of this invention are highly active. For example, the peptide can be administered at 0.01, 0.05, 0.1, 0.5, 1, 5, 10, 50, 100, or 500 μg/kg body weight, depending on specific peptide selected, the desired therapeutic response, the route of administration, the formulation and other factors known to those of skill in the art.

Inflammation and Immune-Mediated Disorders. The compounds of this invention may further be employed in the treatment of inflammation and immune-mediated disorders. See, for example, Catania A. et al, *Trends Endocrinol Metab* 11:304-308, 2000; and Gantz I. and Fong T. M., *Am J Physiol Endocrinol Metab* 284:3468-E474, 2003.

Combination Therapy

It is also possible and contemplated to use peptides of this invention in combination with other drugs or agents, particularly in the treatment of cachexia. These other drugs and agents may include agents that induce weight gain, including corticosteroids and progestational agents. In a preferred embodiment of the invention, peptides of the invention are used in combination with a therapeutically effective amount of a second weight gain pharmaceutical agent.

The present invention thus provides methods treatment of cachexia, the methods comprising the step of administering to the patient having or at risk of having cachexia a therapeutically effective amount of a peptide of this invention in combination with a therapeutically effective amount of another compound that is useful in the treatment of cachexia.

The present invention also provides pharmaceutical compositions that comprise 1) a peptide of this invention, and 2) a second compound useful for the treatment of cachexia.

In an embodiment of the composition above, the additional compounds useful for the treatment of cachexia are preferably selected from but not limited to the group consisting of ADP-ribose-polymerase inhibitors, ADP-ribose-transferase inhibitors, NADase inhibitors, nicotinamide benzamide, theophylline, thymine and analogs thereof; omega-3 fatty acids such as alpha-linolenic acid, stearidonic acid, eicosapentaenoic acid (EPA), docosapentaenoic acid, docosahexaenoic acid or mixtures thereof; branched-chain amino acids valine, leucine, isoleucine or mixtures thereof, with or without reduced levels of tryptophan and 5-hydroxytryptophan; antioxidants selected from the group comprising beta-carotene, vitamin C, vitamin E, selenium, or mixtures thereof; L-glutamine, vitamin A, vitamin C, vitamin E, and selenium; Azaftig; quinine derivatives including 3,5,6-trimethyl-2-(3-pyridyl)methyl-1,4-benzoquinone hydrochloride; interleukin 2; benzaldehyde; 4,6-O-benzylidene-D-glucose; friedelan-3-one; hydrazine sulfate; medroxyprogesterone acetate; beta 2-adrenoceptor agonists; corticosteroids such as dexamethasone; Vitor™; Pro-Stat™; megestrol acetate (Megace™); dronabinol (Marinol™); magestrol acetate (Megace™); thalidomide (Thalidomid™); fluoxymesterone (Halotestin™); pentoxifylline (Trental™); cyproheptadine (Periactin™); metoclopramide (Reglan™); total parenteral nutrition; or other MC4-R antagonists. In another embodiment, the additional compound useful for the treatment of cachexia is somatropin (Serostim™), an injectable form of human growth hormone.

The present invention also provides kits for the treatment of cachexia, the kits comprising: a first pharmaceutical composition including a peptide of this invention; a second pharmaceutical composition comprising a second compound useful for the treatment of cachexia; and, a container for the first and second compositions.

Industrial Applicability:

The invention is further illustrated by the following non-limiting examples.

Example 1

Competitive inhibition assay using [$I^{125}$]-NDP-α-MSH

A competitive inhibition binding assay is conducted using membranes prepared from HEK-293 cells transfected with hMC3-R, hMC4-R or hMC5-R genes, and B-16 mouse melanoma cells (containing MC1-R) using 0.4 nM [$I^{125}$]-NDP-α-MSH (New England Nuclear) in 50 mM HEPES buffer containing 1 mM $MgCl_2$, 2 mM $CaCl_2$, and 5 mM KCl, at pH 7.2. The assay tube also contains a chosen concentration of the test compound of this invention, typically a 1 μM concentration, for determining its efficacy in inhibiting the binding of [$I^{125}$]-NDP-α-MSH to its receptor. Non-specific binding is measured by complete inhibition of binding of [$I^{125}$]-NDP-α-MSH in the assay with the presence of 1 μM α-MSH.

The assay mixture is incubated for 90 minutes at room temperature, then filtered and the membranes washed three times with ice cold buffer. The filter is dried and counted in a gamma counter for remaining radioactivity bound to the membranes. 100% specific binding is defined as the difference in radioactivity (cpm) bound to cell membranes in the absence and presence of 1 μM α-MSH. The cpm obtained in presence of test compounds is normalized with respect to 100% specific binding to determine the percent inhibition of [$I^{125}$]-NDP-α-MSH binding. Each assay is conducted in triplicate. The Ki (nM) of certain compounds of the invention are determined using similar assay protocols and testing compounds over a wider dose range.

Example 2

General Method for $EC_{50}$ Determination in Functional Activity Assay

Functional evaluation of compounds at melanocortin receptors is performed by measuring the accumulation of intracellular cAMP in HEK-293 cells expressing MC3-R, MC4-R or MC5-R, and in B-16 mouse melanoma cells expressing MC1-R. Cells suspended in Earle's Balanced Salt Solution containing 10 mM HEPES (pH 7.5), 5 mM $MgCl_2$, 1 mM glutamine, 0.1% albumin and 0.6 mM 3-isobutyl-1-methyl-xanthine, a phosphodiesterase inhibitor, are plated in 96 well plates at a density of $0.5 \times 10^5$ cells per well. Cells are incubated with the test compounds in the presence or absence of α-MSH for 1 hour at 37° C. cAMP levels in the cell lysates are measured using the EIA kit (Amersham). Data analysis and $EC_{50}$ values are determined using nonlinear regression analysis with Prism Graph-Pad software.

Example 3

Functional Status

The agonist/antagonist status with respect to MC1-R, MC4-R and MC5-R of certain compounds of the invention is determined. Antagonistic activity is determined by measuring the inhibition of α-MSH-induced or NDP-α-MSH-induced cAMP levels following exposure to the compounds as in the preceding descriptions.

Assay for agonist. Evaluation of the molecules to elicit a functional response in HEK-293 cells expressing MC4-R for agonistic activity is done by measuring the accumulation of intracellular cAMP following treatment. Confluent HEK-293 cells over-expressing MC4-R receptors are detached by enzyme free cell suspension buffer. Cells are suspended in Earle's Balanced Salt Solution containing 10 mM HEPES (pH 7.5), 1 mM $MgCl_2$, 1 mM glutamine, 0.5% albumin and 0.3 mM 3-isobutyl-1-methyl-xanthine, a phosphodiesterase inhibitor. The cells are plated in a 96 well plates at a density of $0.5 \times 10^5$ cells per well and pre-incubated for 30 minutes. The cells are then challenged with the test compounds dissolved in dimethylsulfoxide (DMSO) at a concentration range of 0.05-5000 nM in a total assay volume of 200 μL for 1 hour at 37° C. The concentration of DMSO is always held at 1% in the assay mixture. NDP-α-MSH is used as the reference agonist. At the end of the incubation period the cells are disrupted by the addition of 50 μL lysis buffer from the cAMP EIA kit (Amersham). Complete rupture of the cells is ensured by pipetting the cells up and down multiple times. cAMP levels in the cell lysates are measured after appropriate dilution using the EIA kit (Amersham) method. Data analysis and $EC_{50}$ values are determined by using nonlinear regression analysis with the Prism Graph-Pad software. Compounds at a concentration of 500 nM that had a response ratio compared to NDP-α-MSH of 0.7 and above are classified as full agonists. Compounds with a ratio from 0.1 to 0.7 are classified as partial agonists. Compounds with a response ratio of less than 0.1 are evaluated for antagonistic activity.

Assay for Neutral Antagonist. Compounds with a high affinity for binding to MC4-R membranes but with less efficiency ($EC_{50}$>1000 nM) and low response ratio (<0.1) are analyzed for their ability to antagonize the stimulatory effect of the agonist NDP-α-MSH. These studies are carried out in HEK-293 cells expressing MC4-R. Cells are incubated with the compounds in the presence of the agonist NDP-α-MSH and the extent of antagonism is measured by the decrease in intracellular cAMP concentrations. Screening the compounds for antagonists is done at a single concentration of NDP-α-MSH (1.0 nM) over a compound concentration range of 0.5-5000 nM. Studies are extended further in cases of compounds exhibiting strong antagonism to derive the $pA_2$ value from Schild's analysis.

Experimental details are similar to the analysis for agonistic activity and are described above. Briefly, cells are pre-incubated for 30 minutes with the test compounds at concentrations between 0.5 nM and 5000 nM. The cells are then stimulated with NDP-α-MSH at a concentration of 1 nM for 1 hour. For Schild's analysis, the interactions are studied using at least 3 concentrations of the compounds, separated by a log unit, over a full range of the agonist (0.005-5000 nM). cAMP levels is measured in the cell lysates after appropriate dilution. Nonlinear regression analysis with the Prism Graph-Pad software is used for Schild's analysis and to obtain $EC_{50}$ values. $pA_2$ values are derived from the Schild's plot.

Assay for inverse agonist. Compounds that have a weak $EC_{50}$ value ($EC_{50}$>1000 nM) or a low response ratio (<0.1) are also investigated for their ability to act as inverse agonists, i.e. to decrease the basal or constitutive level of cAMP in HEK-293 cells expressing MC4-R. The experimental protocol is essentially the same a described above. The cells are exposed to the test compounds over a concentration range of 0.05 nM to 5000 nM for 1 hour at 37° C. AgRP (83-132) is used as the reference inverse agonist. Data analysis and $EC_{50}$

Example 4

ICV Food Intake and Body Weight Change

Change in food intake and body weight is evaluated for selected compounds. Rats with indwelling intracerebroventricular cannulas (ICV rats) are obtained from Hilltop Lab Animals, Inc. (Scottdale, Pa.). Animals are individually housed in conventional plexiglass hanging cages and maintained on a controlled 12 hour on/off light cycle. Water and powdered (LabDiet, 5P00 Prolab RMH 3000) or pelleted (Harlan Teklad 2018 18% Protein Rodent Diet) food is provided ad libitum. For 1 week before treatment, 24-hour food intake and body weight change is recorded to assess a baseline for the group during vehicle treatment. The rats are dosed ICV with vehicle or selected compounds (1-3 nmol). The changes in body weight and food intake for the 24 hour period after dosing are determined. The changes in body weight and food intake for the 48 hour and 72 hour periods after dosing are also measured to determine reversal of changes in body weight and food intake effects back to baseline levels.

Example 5

IV and IP Food Intake and Body Weight Change

Change in food intake and body weight is evaluated for selected compounds. Male Sprague-Dawley rats are obtained from Taconic (Germantown, N.Y.). Animals are individually housed in conventional plexiglass hanging cages and maintained on a controlled 12 hour on/off light cycle. Water and powdered (LabDiet, 5P00 Prolab RMH 3000) or pelleted (Harlan Teklad 2018 18% Protein Rodent Diet) food is provided ad libitum. For 1 week before treatment, 24-hour food intake and body weight change is recorded to assess a baseline for the group during vehicle treatment. The rats are dosed IV or IP with vehicle or selected compounds (0.5-3 mg/kg). The changes in body weight and food intake for the 24 hour period after dosing are determined. The changes in body weight and food intake for the 48 hour and 72 hour periods after dosing are also measured to determined reversal of changes in body weight and food intake effects back to baseline levels.

Example 6

Behavioral Satiety Sequence

Male Sprague-Dawley rats are maintained on a restricted diet of 20 g powdered food per day. Food is presented at the same time during the lights-on period, dosed with either saline or the test compound 2 hours before presentation of food and the start of observation. Pre-weighed bowls containing 20 g of food are presented and the behavior of the rats is observed for 1 hour. Behavioral observations are divided into 3 categories: Feeding, Active (includes grooming, drinking and sniffing/exploration), and Resting (decreased activity and sleep). The amount of time spent in each behavior is recorded. The amount of food intake is determined after the observation period.

Example 7

Conditioned Taste Avoidance

Male Sprague-Dawley rats are adapted to a restricted drinking period of 30 minutes per day during lights on and are provided with pelleted chow ad libitum. In laboratory animals the administration of LiCl conditions an aversion to the novel and favorable taste of saccharin (Seeley R J, Blake K, Rushing P A, Benoit S, Eng J, Woods S C and D'Alessio D: The role of CNS glucagons-like peptide-1 (7-36) amide receptors in mediating the visceral illness effects of lithium chloride. *J. Neurosci.* 20(4):1616-1621, 2000). To condition animals, an injection of LiCl or test compound is administered immediately after the initial presentation of a 0.1% solution of saccharin. Two days later, saccharin solution is again presented and fluid intake determined. A decrease in drinking the saccharin solution suggests development of a conditioned taste aversion.

Example 8

Lipopolysaccharide-Induced Cachexia Model

Rats with indwelling intracerebroventricular cannulas (ICV rats) are obtained from Hilltop Lab Animals, Inc. (Scottdale, Pa.). Animals are individually housed in conventional plexiglass hanging cages and maintained on a controlled 12 hour on/off light cycle. Water and powdered (LabDiet, 5P00 Prolab RMH 3000) or pelleted (Harlan Teklad 2018 18% Protein Rodent Diet) food are provided ad libitum. LPS (*E. Coli* 055:B5, Sigma Chemical Co.) is dissolved in normal saline and administered i.p. For the first LPS injection, male animals aged 6-7 weeks are used. In an identical repeat experiment, female animals, aged 5 weeks are used. Animals have basal feeding monitored for two days, and then during each twelve hour period following an i.p. saline injection prior to injection of 100 µg/kg of LPS. Certain compounds of the invention are administered, and 50 µg/kg LPS are administered 3 hours later. A second dose of 100 µg/Kg LPS is given 60 hours after the first dose in the second experiment. No food is available between compound administration and LPS administration. Starting after LPS administration, feeding is measured every 6 hours for 24 hours, then every 12 hours for 48 more hours.

In the sham group, basal feeding is measured every six hours in two age and sex-matched groups after simulated ICV injection and i.p. saline injection. Twenty-four hours later, selected compounds are administered, and LPS is administered i.p. 3 hours later. Feeding is measured every 6 hours for 24 hours, then every 12 hours for 48 more hours. The difference between feeding curves in the two groups is expressed both as weight normalized intake and as a percent of basal feeding vs. post-saline and sham icv injection.

Example 9

Tumor-induced Cachexia Model

Lewis lung carcinoma (LLC) cells and Englebreth-Holm-Swarm Sarcoma (EHS) tumors are maintained either as a primary culture in DMEM with 10% fetal bovine serum or in vivo, respectively, as recommended by the supplier. LLC tumor cells are harvested during exponential growth of the culture, washed in Hanks balanced salt solution, and cells are injected subcutaneously into the upper flank of the animals. EHS sarcoma tissue is dissected from a donor animal, and an approximately 3 mm cube of tissue is implanted subcutaneously above the rear flank. Sham operated animals receive an implant of a similar amount of donor muscle tissue. In all cases, the time of appearance of a tumor mass is noted, and all animals are found to have a palpable tumor within four (LLC) or eight (EHS) days of the start of the experiment. At the time of sacrifice, tumors are dissected away from surrounding tissue and weighed. Gross examination of all organs does not reveal the presence of any observable metastasis. Trunk blood is collected at the time of sacrifice for measurement of serum leptin with a rat leptin radioimmunoassay kit.

Animals are individually housed in conventional plexiglass hanging cages and maintained on a controlled 12 hour on/off light cycle. The effects of administration of certain compounds of the invention in animals with hypophagia and weight loss due to the presence of a growing sarcoma are examined. In an initial experiment, daily food intake and weight are followed until the tumor-bearing animals have food intake that is 75-80% of basal for three consecutive days. On average this occurs on day 12 post-implant, or four days after a palpable tumor is present. ICV injection of the selected compounds is performed and animals are monitored to assess the change in food intake.

In a second experiment the ability of selected compounds to prevent the onset of cachexia and maintain normal feeding and growth is tested. Animals are examined daily for the presence of a palpable tumor, with all animals having tumors by day 14 post implantation, and none prior to day 12. Animals are then injected with selected compounds or a sham every 48 hours until sacrifice. A sham-tumor implanted group is included for comparison and is also given the compounds.

Differences between feeding, activity, and water consumption curves in all experiments are analyzed by two-way, repeated measures ANOVA with time and treatment as the measured variables. Final tumor and body weights are analyzed by Student's t-test when two groups are included, or one way ANOVA with post-hoc analysis when three groups are included. Data sets are analyzed for statistical significance using either the PRISM software package (GraphPad) for ANOVA with repeated measures, or in EXCEL (Microsoft) using Student's t-test.

Example 10

Determination of Mass and Nuclear Magnetic Resonance Analysis

The mass values are determined using a Waters MicroMass ZQ device utilizing a positive mode. Mass determinations are compared with calculated values and expressed in the form of mass weight plus one (M+1 or M+H).

Proton NMR data is obtained using a Bruker 300 MHz spectrometer. The spectra are obtained after dissolving compounds in a deuteriated solvent such as chloroform, DMSO, or methanol as appropriate.

Example 11

Peptides of the Invention

Any of the following peptides are synthesized by peptide synthesis methods:
  Ac-Nle-Ala-His-D-NaI 2-Arg-Trp-Lys-OH;
  Ac-Ala-His-D-NaI 2-Arg-Trp-Lys-OH;
  Ac-Nle-Ala-Trp-D-NaI 2-Arg-NaI 2-Lys-OH;
  Ac-Ala-Trp-D-NaI 2-Arg-NaI 2-Lys-OH;
  Ac-Nle-Ala-His-D-NaI 2-Arg-NaI 2-Lys-OH;
  Ac-Ala-His-D-NaI 2-Arg-NaI 2-Lys-OH;
  Nle-Ala-His-D-NaI 2-Arg-Trp-Lys-OH;
  Ala-His-D-NaI 2-Arg-Trp-Lys-OH;
  Nle-Ala-Trp-D-NaI 2-Arg-NaI 2-Lys-OH;
  Ala-Trp-D-NaI 2-Arg-NaI 2-Lys-OH;
  Nle-Ala-His-D-NaI 2-Arg-NaI 2-Lys-OH;
  Ala-His-D-NaI 2-Arg-NaI 2-Lys-OH;
  Succ-His-D-NaI 2-Arg-NaI 2-Lys-OH.
  Ac-Glu-His-D-NaI 2-Arg-Trp-Lys-Pro-Val-OH;
  Ac-Glu-His-D-NaI 2-Arg-Trp-OH;
  Ac-Glu-Pro-D-NaI 2-Arg-Trp-OH;
  Ac-Ala-Nle-Arg-His-D-NaI 2-Arg-Trp-Gly-OH;
  Nle-Arg-His-D-NaI 2-Arg-Trp-Gly-OH;
  Ac-Glu-His-D-NaI 2-Arg-Trp-Pro-Pro-Lys-Asp-OH;
  Ac-Glu-Pro-D-NaI 2-Arg-Trp-Pro-Pro-Lys-Asp-OH;
  Ac-His-D-NaI 2-Arg-Trp-OH;
  Ac-His-D-NaI 2-Arg-Trp-Lys-OH;
  Ac-Trp-D-NaI 2-Arg-NaI 2-OH;
  Ac-Trp-D-NaI 2-Arg-NaI 2-Lys-OH;
  Ac-His-D-NaI 2-Arg-NaI 2-OH;
  Ac-His-D-NaI 2-Arg-NaI 2-Lys-OH;
  Ac-Pro-D-NaI 2-Arg-NaI 2-OH;
  Ac-Pro-D-NaI 2-Arg-NaI 2-Lys-OH;
  His-D-NaI 2-Arg-Trp-OH;
  His-D-NaI 2-Arg-Trp-Lys-OH;
  Trp-D-NaI 2-Arg-NaI 2-OH;
  Trp-D-NaI 2-Arg-NaI 2-Lys-OH;
  His-D-NaI 2-Arg-NaI 2-OH;
  His-D-NaI 2-Arg-NaI 2-Lys-OH;
  Pro-D-NaI 2-Arg-NaI 2-OH;
  Pro-D-NaI 2-Arg-NaI 2-Lys-OH; or
  Succ-His-D-NaI 2-Arg-NaI 2-OH.

The molecular weight is determined. Competitive inhibition testing and Ki (nM) of the compound is measured following the method of Example 1. Functional status of the compound is determined following the methods of Examples 2 and 3. Efficacy in animal models is determined following the methods of Examples 4 through 9.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

What is claimed is:

1. A linear peptide of the formula:

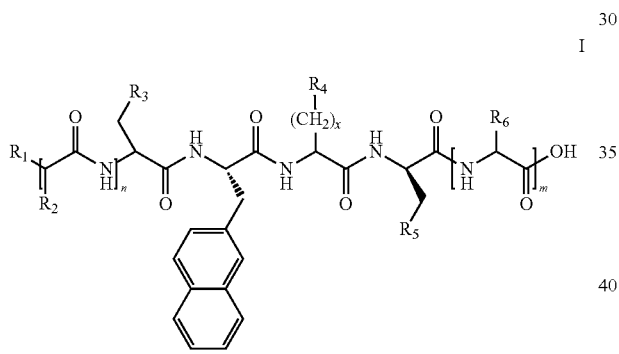

wherein:

$R_1$ is H, $NH_2$,

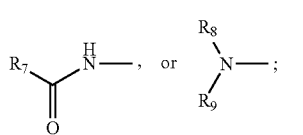

$R_2$ is in each instance independently an amino acid side chain moiety;

$R_3$ is 4-imidazolyl, 3-indolyl, 2-pyrrolidine, phenyl, or 1- or 2-naphthyl, optionally with one or two ring substituents, and when one or both ring substitutents are present, are the same or different and independently hydroxyl, halogen, alkyl, or aryl groups attached directly or through an ether linkage;

$R_4$ is $-NH_2$, $-NH-(CH_2)_y-NH_2$, or $-NH-(C=NH)-NH_2$;

$R_5$ is 1- or 2-naphthyl, optionally with one or two ring substituents, and when one or both ring substituents are present, are the same or different and independently hydroxyl, halogen, alkyl, or aryl groups attached directly or through an ether linkage;

$R_6$ is in each instance independently H or an amino acid side chain moiety;

$R_7$ is H, $NH_2$, a lower aliphatic $C_1$ to $C_4$ linear or branched alkyl chain, a $C_1$ to $C_4$ aralkyl, or a $C_1$ to $C_4$ omega amino derivative;

$R_8$ is H, a lower aliphatic $C_1$ to $C_4$ linear or branched alkyl chain, a $C_1$ to $C_4$ aralkyl, a $C_1$ to $C_4$ linear alkyl chain with an N-terminus carboxyl group, or a $C_1$ to $C_4$ omega amino derivative;

$R_9$ is a linear or branched $C_1$ to $C_{17}$ alkyl, aryl, heteroaryl, alkene, alkenyl, or aralkyl chain;

n is from 0 to 3;

m is from 0 to 7;

x is 2 to 5; and y is 1 to 3.

2. The peptide of claim 1 wherein $R_1$ is

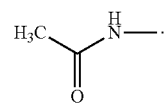

3. The peptide of claim 2 wherein n is 0.

4. The peptide of claim 2 wherein n is 1 and $R_2$ is an amino acid side chain moiety of Nle or Ala.

5. The peptide of claim 2 wherein n is 2 and $R_2$ is in each instance an amino acid side chain moiety of Nle, Ala, Arg, or a combination thereof.

6. The peptide of claim 1 wherein $R_1$ is

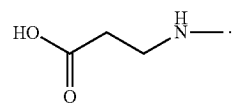

7. The peptide of claim 1 wherein m is 1 and $R_6$ is H or an amino acid side chain moiety of Lys.

8. The peptide of claim 1 wherein m is 2 and $R_6$ is H or an amino acid side chain moiety of Lys or Trp or a combination thereof.

9. The peptide of claim 1 wherein m is 3 or 4 and $R_6$ is H or an amino acid side chain moiety of Lys Val Asp or Trp or a combination thereof.

10. The peptide of claim 1 which is:
Ac-Nle-Ala-Trp-D-NaI 2-Arg-NaI 2-Lys-OH;
Ac-Ala-Trp-D-NaI 2-Arg-NaI 2-Lys-OH;
Ac-Nle-Ala-His-D-NaI 2-Arg-NaI 2-Lys-OH;
Ac-Ala-His-D-NaI 2-Arg-NaI 2-Lys-OH;
Nle-Ala-Trp-D-NaI 2-Arg-NaI 2-Lys-OH;
Ala-Trp-D-NaI 2-Arg-NaI 2-Lys-OH;
Nle-Ala-His-D-NaI 2-Arg-NaI 2-Lys-OH;
Ala-His-D-NaI 2-Arg-NaI 2-Lys-OH;
Succ-His-D-NaI 2-Arg-NaI 2-Lys-OH;
Ac-Trp-D-NaI 2-Arg-NaI 2-OH;
Ac-Trp-D-NaI 2-Arg-NaI 2-Lys-OH;
Ac-His-D-NaI 2-Arg-NaI 2-OH;
Ac-His-D-NaI 2-Arg-NaI 2-Lys-OH;
Trp-D-NaI 2-Arg-NaI 2-OH;
Trp-D-NaI 2-Arg-NaI 2-Lys-OH;
His-D-NaI 2-Arg-NaI 2-OH;
His-D-NaI 2-Arg-NaI 2-Lys-OH; or
Succ-His-D-NaI 2-Arg-NaI 2-OH.

11. A linear peptide of the formula:

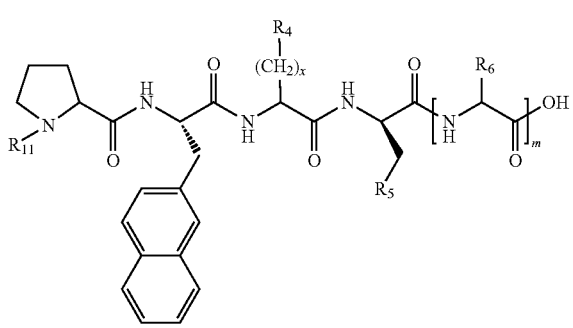

II wherein:
$R_{11}$ is H or

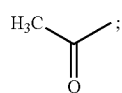

$R_4$ is $-NH_2$, $-NH-(CH_2)_y-NH_2$, or $-NH-(C=NH)-NH_2$;

$R_5$ is 1- or 2-naphthyl, optionally with one or two ring substituents, and when one or both ring substitutents are present, are the same or different and independently hydroxyl, halogen, alkyl, or aryl groups attached directly or through an ether linkage;

$R_6$ is in each instance independently H or an amino acid side chain moiety;

m is from 0 to 7; and x is 2 to 5.

12. The peptide of claim 11 which is:
Ac-Pro-D-NaI 2-Arg-NaI 2-OH;
Ac-Pro-D-NaI 2-Arg-NaI 2-Lys-OH;
Pro-D-NaI 2-Arg-NaI 2-OH; or
Pro-D-NaI 2-Arg-NaI 2-Lys-OH.

13. A linear peptide which is:
Ac-Nle-Ala-His-D-NaI 2-Arg-Trp-Lys-OH;
Ac-Ala-His-D-NaI 2-Arg-Trp-Lys-OH;
Ac-Nle-Ala-Trp-D-NaI 2-Arg-NaI 2-Lys-OH;
Ac-Ala-Trp-D-NaI 2-Arg-NaI 2-Lys-OH;
Ac-Nle-Ala-His-D-NaI 2-Arg-NaI 2-Lys-OH;
Ac-Ala-His-D-NaI 2-Arg-NaI 2-Lys-OH;
Nle-Ala-His-D-NaI 2-Arg-Trp-Lys-OH;
Ala-His-D-NaI 2-Arg-Trp-Lys-OH;
Nle-Ala-Trp-D-NaI 2-Arg-NaI 2-Lys-OH;
Ala-Trp-D-NaI 2-Arg-NaI 2-Lys-OH;
Nle-Ala-His-D-NaI 2-Arg-NaI 2-Lys-OH;
Ala-His-D-NaI 2-Arg-NaI 2-Lys-OH;
Succ-His-D-NaI 2-Arg-NaI 2-Lys-OH;
Ac-Glu-His-D-NaI 2-Arg-Trp-Lys-Pro-Val-OH;
Ac-Glu-His-D-NaI 2-Arg-Trp-OH;
Ac-Glu-Pro-D-NaI 2-Arg-Trp-OH;
Ac-Ala-Nle-Arg-His-D-NaI 2-Arg-Trp-Gly-OH;
Nle-Arg-His-D-NaI 2-Arg-Trp-Gly-OH;
Ac-Glu-His-D-NaI 2-Arg-Trp-Pro-Pro-Lys-Asp-OH;
Ac-Glu-Pro-D-NaI 2-Arg-Trp-Pro-Pro-Lys-Asp-OH;
Ac-His-D-NaI 2-Arg-Trp-OH;
Ac-His-D-NaI 2-Arg-Trp-Lys-OH;
Ac-Trp-D-NaI 2-Arg-NaI 2-OH;
Ac-Trp-D-NaI 2-Arg-NaI 2-Lys-OH;
Ac-His-D-NaI 2-Arg-NaI 2-OH;
Ac-His-D-NaI 2-Arg-NaI 2-Lys-OH;
Ac-Pro-D-NaI 2-Arg-NaI 2-OH;
Ac-Pro-D-NaI 2-Arg-NaI 2-Lys-OH;
His-D-NaI 2-Arg-Trp-OH;
His-D-NaI 2-Arg-Trp-Lys-OH;
Trp-D-NaI 2-Arg-NaI 2-OH;
Trp-D-NaI 2-Arg-NaI 2-Lys-OH;
His-D-NaI 2-Arg-NaI 2-OH;
His-D-NaI 2-Arg-NaI 2-Lys-OH;
Pro-D-NaI 2-Arg-NaI 2-OH;
Pro-D-NaI 2-Arg-NaI 2-Lys-OH; or
Succ-His-D-NaI 2-Arg-NaI 2-OH.

* * * * *